US00PP27268P2

(12) United States Plant Patent
Klemm et al.

(10) Patent No.: US PP27,268 P2
(45) Date of Patent: Oct. 11, 2016

(54) ***OSTEOSPERMUM* PLANT NAMED 'KLEOE14235'**

(50) Latin Name: ***Osteospermum ecklonis* Norl**
Varietal Denomination: KLEOE14235

(71) Applicant: Klemm+Sohn GmbH & Co. KG, Stuttgart (DE)

(72) Inventors: Nils Klemm, Stuttgart (DE); Silke Wagener, Leinfelden-Echterdingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 79 days.

(21) Appl. No.: 14/545,027

(22) Filed: Mar. 18, 2015

(51) Int. Cl.
*A01H 5/02* (2006.01)

(52) U.S. Cl.
USPC ..... Plt./360

(58) Field of Classification Search
USPC ..... Plt./360
See application file for complete search history.

*Primary Examiner* — June Hwu
(74) *Attorney, Agent, or Firm* — Bethany R. Roahrig; James M. Weatherly; Cochran Freund & Young, LLC

(57) ABSTRACT

A new *osteospermum* plant particularly distinguished by light violet ray florets with a lighter violet ring and darker at the base, and a semi-upright growth habit, is disclosed.

1 Drawing Sheet

Genus and species: *Osteospermum ecklonis* Norl.
Variety denomination: 'KLEOE14235'.

BACKGROUND OF THE NEW PLANT

The present invention comprises a new and distinct variety of *osteospermum*, botanically known as *Osteospermum ecklonis* Norl, and hereinafter referred to by the variety name 'KLEOE14235'. 'KLEOE14235' originated from a cross-pollination conducted in the summer of 2009 in Stuttgart, Germany between the proprietary female *osteospermum* variety '0E-2006-0062' (unpatented), and the proprietary male *osteospermum* variety 'OE-2001-U 088' (unpatented).

The seeds from the cross were sown and plants were grown in a greenhouse for evaluation, where an individual plant designated 'KLEOE14235' was selected from the group of plants in April 2011 in Stuttgart, Germany. In May 2011 in Stuttgart, Germany, 'KLEOE14235' was first vegetatively propagated by terminal cuttings. 'KLEOE14235' was found to reproduce true to type in successive generations of asexual propagation via terminal cuttings.

SUMMARY

The following are the most outstanding and distinguishing characteristics of this new variety when grown under normal horticultural practices in Stuttgart, Germany.

1. Light violet ray florets with a lighter violet ring and darker at the base; and
2. A semi-upright growth habit.

DESCRIPTION OF THE PHOTOGRAPH

This new *osteospermum* plant is illustrated by the accompanying photograph which shows the plant's overall plant habit including form, foliage, and flowers. The photograph is of a three-month-old plant grown in a greenhouse in Stuttgart, Germany in June 2012. The colors shown are as true as can be reasonably obtained by conventional photographic procedures.

DESCRIPTION OF THE NEW VARIETY

The following detailed descriptions set forth the distinctive characteristics of 'KLEOE14235'. The data which define these characteristics were collected from asexual reproductions carried out in Stuttgart, Germany. Data was collected on 5-month-old plants grown in a greenhouse using a growth regulation of tilt 0.5% and 0.8% several times in Stuttgart, Germany in March 2015. Color references are to The R.H.S. Colour Chart of The Royal Horticultural Society of London (R.H.S.), 5$^{th}$ edition (2007).

Classification:
- *Family.*—Asteraceae.
- *Botanical.*—*Osteospermum ecklonis* Norl.
- *Common.*—African Daisy.
- *Designation.*—'KLEOE14235'.

Parentage:
- *Female parent.*—The proprietary *osteospermum* variety '0E-2006-0062' (unpatented).
- *Male parent.*—The proprietary *osteospermum* variety '0E-2001-U 088' (unpatented).

Plant:
- *Form and habit.*—Herbaceous perennial but usually cultivated as an annual; not frost resistant.
- *Growth habit.*—Semi-upright.
- *Branching habit.*—Freely branching.
- *Height (from top of soil, including inflorescence).*—About 30.0 cm.
- *Width (including inflorescences).*—About 25.0 cm.
- *Propagation.*—Terminal cuttings.
- *Time to produce a finished flowering plant.*—14 weeks (in the spring and winter).
- *Time to initiate and develop roots.*—3 weeks.
- *Root description.*—Freely rooting, light tan in color.

Leaves:
- *Arrangement.*—Alternate.
- *Shape.*—Obovate.

*Apex.*—Broadly acute.
*Base.*—Narrowly acute.
*Margin.*—Shallow.
*Immature color.*—Upper surface: RHS 143A. Lower surface: RHS 143B.
*Mature color.*—Upper surface: RHS 141A. Lower surface: RHS 139B.
*Length.*—Up to 7.0 cm.
*Width.*—Up to 3.0 cm.
*Texture and appearance.*—Upper surface: Shiny leathery. Lower surface: Pubescent; covering of fine hairs.
*Petioles.*—Absent.
*Venation pattern.*—Pinnate.
*Venation color* (*both upper and lower surfaces*).—RHS 143C.

Stems:
*Total number of branches per plant* (*calculated at the base of the plant*).—5.
*Length.*—Up to 20.0 cm.
*Diameter.*—0.6 cm.
*Internode length.*—About 1.5 cm.
*Color.*—RHS 143C.
*Texture.*—Shiny, smooth.
*Anthocyanin.*—Absent.

Flower buds:
*Shape.*—Round-ovoid.
*Length.*—About 1.0 cm.
*Diameter.*—About 1.0 cm.
*Color* (*at tight bud just before the ray florets unfold*) .—RHS 143A.

Inflorescence:
*Type.*—Composite, single.
*Blooming habit.*—Spring to autumn.
*Quantity of inflorescences per plant.*—30 to 40.
*Lastingness of the inflorescences on the plant.*—About 2 weeks.
*Fragrance.*—Absent to faint.
*Inflorescence diameter.*—About 6.0 cm.
*Inflorescence depth.*—1.0 cm to 1.5 cm.
*Disc diameter.*—About 1.7 cm.

Disc floret:
*Quantity per inflorescence.*—About 110.
*Shape.*—Oblanceolate.
*Tube color.*—Closed: RHS 139D. Mature: RHS 93B.
*Length.*—About 0.5 cm.
*Diameter* (*at apex*).—About 0.1 cm.
*Apex.*—Obtuse.
*Apex color.*—RHS 93B.
*Base.*—Acute.
*Base color.*—RHS 155C.
*Margin.*—Entire.

Ray floret:
*Quantity per inflorescence.*—About 22.
*Shape.*—Oblanceolate.
*Color.*—Upper surface: Apical and middle part RHS 84B, basal RHS 84C, darker ring at base RHS N80B, and end of flowering RHS N78B. Lower surface: RHS N82A.
*Length.*—About 2.5 cm.
*Width.*—1.8 cm.
*Apex.*—Obtuse.
*Base.*—Acute.
*Margin.*—Entire.
*Texture.*—Upper surface: Smooth. Lower surface: Smooth, shiny.

Peduncle:
*Length.*—Up to 8.0 cm.
*Diameter.*—About 0.2 cm.
*Texture.*—Pubescent; covering of fine hairs.
*Color.*—RHS 143C.

Phyllaries:
*Texture.*—Pubescent; covering of fine hairs.
*Arrangement.*—Single.
*Observed quantity per flower.*—About 20.
*Shape.*—Lanceolate.
*Color.*—Outer surface: RHS 143A. Inner surface: RHS 143B.
*Length.*—Between 0.7 cm and 1.2 cm.
*Width.*—Up to 0.4 cm.
*Apex.*—Narrowly acute.
*Base.*—Acute.
*Margin.*—Entire.
*Texture.*—Outer surface: Pubescent; covering of fine hairs. Inner surface: Shiny.

Reproductive organs:
*Androecium.*—Location: On the disc floret. Stamens: Quantity: Numerous. Shape: Filamentous. Filament length: About 0.4 cm. Filament diameter: Less than 0.05 cm. Anther: Shape: Lanceolate. Color: RHS N92A. Length: About 0.2 cm. Diameter: Less than 0.05 cm. Pollen: Color: RHS 14A. Amount: Moderate.
*Gynoecium.*—Location: On the base of the petals (ray floret), reduced on disc florets. Pistils: Number: About 22 per flower, one per petal. Length: About 0.5 cm. Diameter: Less than 0.05 cm. Stigma: Color: RHS N92A. Shape: Split in two parts at the end. Length: About 0.2 cm. Diameter: Less than 0.05 cm. Style: Color: RHS 76B. Length: About 0.3 cm. Diameter: 0.05 cm.

Fruit and seed set: None observed.
Disease and pest/insect resistance: None observed.

COMPARISON WITH PARENTAL LINES AND KNOWN VARIETY

'KLEOE14235' is a distinct variety of *osteospermum* and is distinguished from its parents as described in Table 1.

TABLE 1

Comparison with Parental Lines

| Characteristic | 'KLEOE14235' | Female Parent 'OE-2006-0062' | Male Parent 'OE-2001-U 088' |
|---|---|---|---|
| Ray floret color | Light violet with lighter violet ring basal and darker at base | Pink-violet | Pink with very broad white ring |

'KLEOE14235' is most similar to the commercial *osteospermum* variety 'KLEOE05115' (U.S. Plant Pat. No. 18,634). Differences between the varieties are described in Table 2.

TABLE 2

Comparison with Similar Variety

| Characteristic | 'KLEOE14235' | 'KLEOE05115' |
|---|---|---|
| Plant height | Short to medium; about 30.0 cm tall | Medium to tall; about 40.0 cm tall |

We claim:

1. A new and distinct variety of *osteospermum* plant designated 'KLEOE14235' as illustrated and described herein.

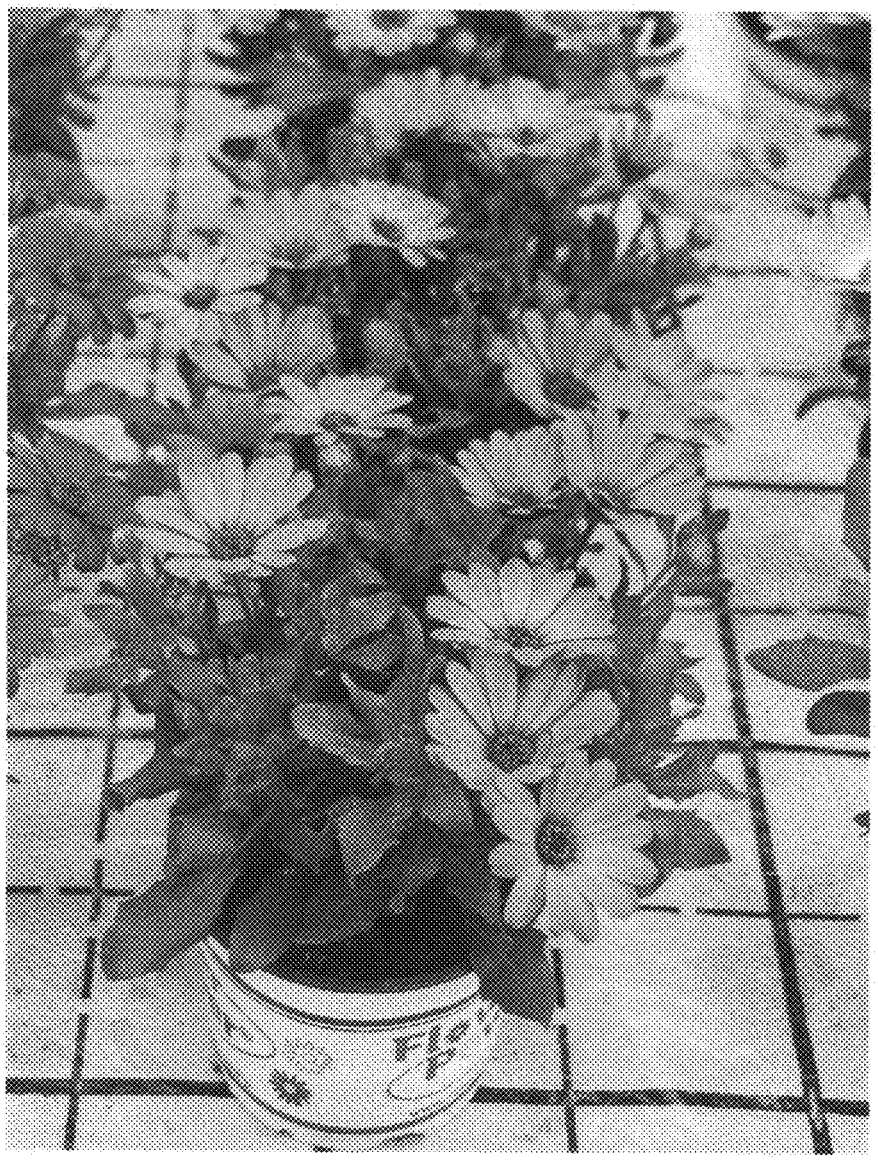

* * * * *